(12) United States Patent
Jong et al.

(10) Patent No.: US 7,115,788 B2
(45) Date of Patent: Oct. 3, 2006

(54) METHOD FOR THE PREPARATION OF α,α,α',α'-TETRAFLUORO-P-XYLENE

(75) Inventors: Shean Jeng Jong, Chungho (TW); Hong Yu Hsu, Taipei (TW)

(73) Assignee: Welsum Enterprise Co., Ltd., Taipei (TW)

(*) Notice: Subject to any disclaimer, the term of this patent is extended or adjusted under 35 U.S.C. 154(b) by 295 days.

(21) Appl. No.: 10/870,984

(22) Filed: Jun. 21, 2004

(65) Prior Publication Data

US 2005/0283031 A1   Dec. 22, 2005

(51) Int. Cl.
*C07C 22/08* (2006.01)

(52) U.S. Cl. .............................. 570/143; 1/123; 1/144; 1/145

(58) Field of Classification Search ................ 570/123, 570/143, 144, 145, 1
See application file for complete search history.

(56) References Cited

FOREIGN PATENT DOCUMENTS

WO    WO98/24743    *   6/1998

* cited by examiner

*Primary Examiner*—Johann Richter
*Assistant Examiner*—Lansana Nyalley
(74) *Attorney, Agent, or Firm*—Leong C. Lei

(57) ABSTRACT

A method for the preparation of α,α,α',α'-tetrafluoro-p-xylene is disclosed. α,α,α',α'-tetrachloro-p-xylene and KF and a small amount of phase transfer catalyst are dissolved in solvent, xylene, and undergo a recycle reaction for 48 hours, after which 60% of the product is obtained

1 Claim, No Drawings

METHOD FOR THE PREPARATION OF α,α,α',α'-TETRAFLUORO-P-XYLENE

BACKGROUND OF THE INVENTION (a) Technical Field of the Invention

The present invention relates to a method of preparation of α,α,α',α'-tetrafluoro-p-xylene, in particular, to a preparation method using α,α,α',α'-tetrafluoro-p-xylene and KF with phase transfer catalyst.

(b) Description of the Prior Art

Russian Patent No. Ru 2032654 (1995) discloses the preparation of α,α,α',α'-tetrafluoro-p-xylene by reacting α,α,α',α'-tetrabromo-p-xylene and SbF$_3$ at 100–150° C./20–100 mm Hg. The methods of preparation of α,α,α', α'-tetrafluoro-p-xylene are as follows:

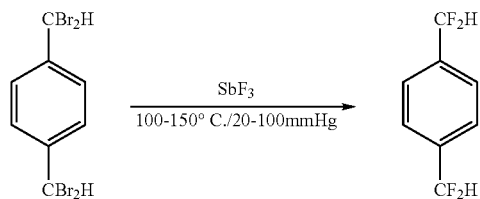

EP No. 949663 (1999) discloses the preparation of α,α, α',α'-tetrafluoro-p-xylene by reacting terephthol aldehyde and 1,2-ethanedithiol, and then with HF/pyridine, under reduced pressure and distillation. The reaction is as follows:

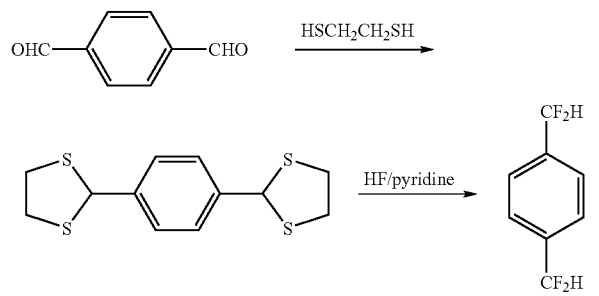

α,α,α',α'-tetrafluoro-p-xylene by reacting α,α,α',α'-tetrachloro-p-xylene with HF at 70° C., 7 kg/cm². The reaction is as follows:

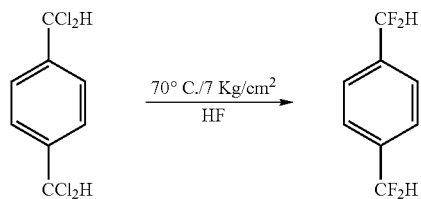

EP Patent No. 970938 (2000) discloses the preparation of α,α,α',α'-tetrafluoro-p-xylene by reacting para-phthalic aldehyde with SF$_4$/HF. The reaction is as follows:

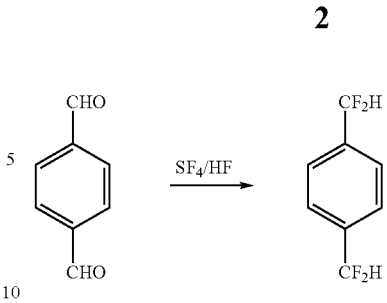

WO9824743 (1998) by Dolbier, William R., Jr., Rong, Xiao X., Stalzer, Walter E, discloses the preparation of α,α,α',α'-tetrafluoro-p-xylene by stirring α,α,α',α'-tetrachloro-p-xylene with alkali metal fluoride such as potassium fluoride at high temperature without solvent. The reaction is as follows:

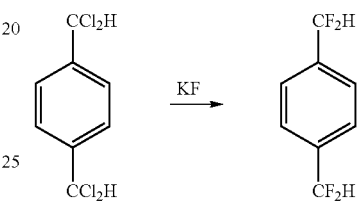

In this method, the alkaline fluoride is cheap and stable. But it has a difficulty in stirring. When α,α,α',α'-tetrachloro-p-xylene is 8 equivalent of KF, and without stirring, it takes 7 days to react under 240° C. In addition the yield is about 54%, and a partial of the fluoride will be decomposed and it forms a lump with the metallic salt, which is difficult to dissolve in water and organic solvent such as hexane, ether, ketone, methanol, ethanol, CH$_2$Cl$_2$, CH$_3$Cl, CCl$_4$, THF, dioxane, NMP, OMF, acetic acid, ethyl ester, benzene, phenyl, etc. Thus, it is difficult to clean the reactor.

SUMMARY OF THE INVENTION

Accordingly, it is an object of the present invention is to provide a method of preparing α,α,α',α'-tetrafluoro-p-xylene comprising the steps of recycling reaction of a α,α,α', α'-tetrachloro-p-xylene and alkaline metal fluoride and a phase transfer catalyst in xylene to obtain the desired product, α,α,α',α'-tetrafluoro-p-xylene, wherein the fluoride reagent is MF wherein M is selected from the group consisting of Li, Na, K, Cs, preferably K is selected, and the amount ranges from 1 to 100 times of α,α,α',α'-tetrachloro-p-xylene mole number, and the solvent for α,α,α',α'-tetrafluoro-p-xylene is o-xylene, m-xylene, p-xylene, or xylene, and preferably xylene, and the amount ranges from 0.01 to 10 kg/mole with respect to mole number of α,α,α', α'-tetrafluoro-p-xylene, and the phase transfer catalyst is Ph$_4$PX and X is selected from the group consisting of Cl, Br, I, preferably Cl, and the amount ranges from 0.1 to 1000 g/mole with respect to mole number of α,α,α',α'-tetrafluoro-p-xylene, and the reaction temperature is from 25 to 400°.

Yet another object of the present invention is to provide the method for the preparation of α,α,α',α'-tetrafluoro-p-xylene is 60%.

Still another object of the present invention is to provide the method for the preparation of α,α,α',α'-tetrafluoro-p-xylene, wherein solvent reaction is applied and the stirring process is easy, and the discarded salt product does not formed into block and can be easily removed.

The foregoing object and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

The following descriptions are of exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

The present invention relates to a method of preparing $\alpha,\alpha,\alpha',\alpha'$-tetrafluoro-p-xylene comprising the steps of recycling reaction of a $\alpha,\alpha,\alpha',\alpha'$-tetrachloro-p-xylene and alkaline metal fluoride and a phase transfer catalyst in xylene to obtain the desired product, $\alpha,\alpha,\alpha',\alpha'$-tetrafluoro-p-xylene, wherein the fluoride reagent is MF wherein M is selected from the group consisting of Li, Na, K, Cs, preferably K is selected, and the amount ranges from 1 to 100 times of $\alpha,\alpha,\alpha',\alpha'$-tetrachloro-p-xylene mole number, and the solvent for $\alpha,\alpha,\alpha',\alpha'$-tetrafluoro-p-xylene is o-xylene, m-xylene, p-xylene, or xylene, and preferably xylene, and the amount ranges from 0.01 to 10 kg/mole with respect to mole number of $\alpha,\alpha,\alpha',\alpha'$-tetrafluoro-p-xylene, and the phase transfer catalyst is $Ph_4PX$ and X is selected from the group consisting of Cl, Br, I, preferably Cl, and the amount ranges from 0.1 to 1000 g/mole with respect to mole number of $\alpha,\alpha,\alpha',\alpha'$-tetrafluoro-p-xylene, and the reaction temperature is from 25 to 400°.

In accordance with the present invention, Cl is a preferred phase transfer catalyst and the amount ranges from 0.1 to 1000 g/mole with respect to mole number of $\alpha,\alpha,\alpha',\alpha'$-tetrafluoro-p-xylene, preferably 25 g/mole.

The following examples are used to further elaborate the present invention and are not limited to the scope of the present invention.

EXAMPLE 1

Xylene was used as solvent, a magnetic stirrer was employed and the reaction was carried out at recycling temperature 47.5 g of KF (0.82 mole) was placed in a 100 ml round conical flask. Under 200° C. and at reduced pressure, the flask was vacuumed and dried for 2 hours. After the flask was cooled to a room temperature, 25 g (0.1 mole) of $\alpha,\alpha,\alpha',\alpha'$-tetrachloro-p-xylene, under nitrogen, 25 g of xylene and 25 g of tetraphenylphospho nium chloride were introduced into the flask. Under nitrogen, the compositions were stirred and recycling reacted for 2 days. The obtained product was 60% of $\alpha,\alpha,\alpha',\alpha'$-tetrafluoro-p-xylene, 1.3% of $\alpha$-chloro, $\alpha,\alpha',\alpha'$-tetrafluoro-p-xylene, and 18.2% of $\alpha$-dichlorod', p-xylene, $\alpha$-difluoro-p-xylene.

COMPARATIVE EXAMPLE 1

(No solvent, no stirring, 400° C. reaction temperature)

95 g (1.6 mole) of KF was placed in a 250 ml conical flask. Under 200° C. and at a reduced pressure, the flask was vacuum and dried for 2 hour until room temperature. Under nitrogen, 50 g 0.2 mole) of $\alpha,\alpha,\alpha',\alpha'$-tetrachloro-p-xylene was introduced under nitrogen and reacted at 400° C. for 4 hour to obtain 9.8% $\alpha,\alpha,\alpha',\alpha'$-tetrafluoro-p-xylene. Other products were 20% $\alpha$-chloro, $\alpha,\alpha',\alpha'$-trifluoro-p-xylene, and 28% trichloro-p-xylene and 5.9% $\alpha,\alpha,\alpha',\alpha'$-tetrachloro-p-xylene. When the reacting time increased, the yield of $\alpha,\alpha,\alpha',\alpha'$-tetrafluoro-p-xylene reduced and decomposed. At 400° C. insoluble solid increased until a white solid was obtained.

COMPARATIVE EXAMPLE II (No solvent, no stirring, 350° C. reaction temperature)

95 g (1.6 mole) of KF was placed in a 250 ml conical flask. Under 200° C. and at a reduced pressure, the flask was vacuum and dried for 2 hour until room temperature. Under nitrogen, 50 g (0.2 mole) of $\alpha,\alpha,\alpha',\alpha'$-tetrachloro-p-xylene was introduced under nitrogen and reacted at 350° C. for 12 hour to obtain 18.3% $\alpha,\alpha,\alpha',\alpha'$-tetrafluoro-p-xylene. Other products were 28.1% $\alpha$-chloro, $\alpha,\alpha',\alpha'$-trifluoro-p-xylene, and 28% trichloro-p-xylene and 5.9% $\alpha,\alpha,\alpha',\alpha'$-tetrachloro-p-xylene and 27.3% $\alpha,\alpha$-dichloro, $\alpha',\alpha'$-difluoro-p-xylene, 6.6% $\alpha$-fluoro, $\alpha,\alpha',\alpha'$-trichloro-p-xylene and 1% $\alpha,\alpha,\alpha',\alpha'$-tetrachloro-p-xylene. When the reacting time increased, the yield of $\alpha,\alpha,\alpha',\alpha'$-tetrafluoro-p-xylene reduced and decomposed. At 350° C. insoluble solid increased until a white solid was obtained

COMPARATIVE EXAMPLE III (No solvent, no stirring, reaction temperature 300° C.)

95 g (1.6 mole) of KF was placed in a 250 ml conical flask. Under 200° C. and at a reduced pressure, the flask was vacuum and dried for 2 hour until room temperature. Under nitrogen, 50 g 0.2 mole) of $\alpha,\alpha,\alpha',\alpha'$-tetrachloro-p-xylene was introduced under nitrogen and reacted at 300° C. for 24 hours to obtain 36.6% $\alpha,\alpha,\alpha',\alpha'$-tetrafluoro-p-xylene. Other products were 31.9% $\alpha$-chloro, $\alpha,\alpha',\alpha'$-trifluoro-p-xylene, and 9.7% trichloro-p-xylene and 1.3% $\alpha$-fluoro, $\alpha,\alpha',\alpha'$-trichloro-p-xylene. When the reacting time increased, the yield of $\alpha,\alpha,\alpha',\alpha'$-tetrafluoro-p-xylene reduced and decomposed. At 300° C. insoluble solid increased until a white solid was obtained.

COMPARATIVE EXAMPLE IV (No solvent, no stirring, reaction temperature 240° C.)

600 g (10.34 mole) of KF was placed in a 2-l conical flask. Under 200° C. and reduced pressure, the flask was vacuum and dried for 2 hour till cold. Under nitrogen condition, 300 g (1.23 mole) of $\alpha,\alpha,\alpha',\alpha'$-tetrachloro-p-xylene was reacted at 240° C. for 168 hours. 54% of $\alpha,\alpha,\alpha',\alpha'$-tetrafluoro-p-xylene was obtained. Others were 17% $\alpha$-chloro, $\alpha,\alpha',\alpha'$-trifluoro-p-xylene, and 10% $\alpha,\alpha$-dichloro, $\alpha',\alpha'$-difluoror-p-xylene. When the reaction time was decreased or increased, the yield of $\alpha,\alpha,\alpha',\alpha'$-tetrafluoro-p-xylene was reduced. If the reaction temperature was below 200° C., similarly the yield of α,α,α',α'-tetrafluoro-p-xylene was reduced and the unreacted α,α,α',α'-teraafluoro-p-xylene was increased.

It will be understood that each of the elements described above, or two or more together may also find a useful application in other types of methods differing from the type described above.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the spirit of the present invention.

We claim:

1. A method of preparing α,α,α',α'-tetrafluoro-p-xylene comprising the steps of: reaction of an α,α,α',α'-tetrachloro-p-xylene with alkaline metal fluoride and a phase transfer catalyst in xylene to obtain α,α,α',α'-tetrafluoro-p-xylene, wherein fluoride reagent for α,α,α',α'-tetrafluoro-p-xylene is MF and M is selected from a group consisting of Li, Na, K and Cs, and the amount ranges from 1 to 100 times of α,α,α',α'-tetrachloro-p-xylene mole number, and solvent for α,α,α',α'-tetrafluoro-p-xylene is selected from a group consisting of o-xylene, m-xylene, p-xylene, and xylene, and the amount ranges from 0.01 to 10 kg/mole with respect to mole number of α,α,α',α'-tetrafluoro-p-xylene, and the phase transfer catalyst is $Ph_4PX$ and X is selected from a group consisting of Cl, Br and I, and the amount ranges from 0.1 to 1000 g/mole with respect to mole number of α,α,α',α'-tetrafluoro-p-xylene, and reaction temperature is from 25 to 400° C.

* * * * *